United States Patent
Miyazono

(10) Patent No.: US 10,777,881 B2
(45) Date of Patent: Sep. 15, 2020

(54) RECEIVING ANTENNA, RECEIVING ANTENNA UNIT, AND RECEIVING SYSTEM

(71) Applicant: OLYMPUS CORPORATION, Tokyo (JP)

(72) Inventor: Toru Miyazono, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 16 days.

(21) Appl. No.: 16/377,382

(22) Filed: Apr. 8, 2019

(65) Prior Publication Data

US 2019/0237863 A1 Aug. 1, 2019

Related U.S. Application Data

(63) Continuation of application No. PCT/JP2017/034279, filed on Sep. 22, 2017.

(30) Foreign Application Priority Data

Oct. 14, 2016 (JP) ................. 2016-202705

(51) Int. Cl.
*H01Q 1/48* (2006.01)
*H01Q 1/27* (2006.01)
(Continued)

(52) U.S. Cl.
CPC ............. *H01Q 1/48* (2013.01); *A61B 1/00* (2013.01); *H01Q 1/273* (2013.01); *H04B 1/18* (2013.01);
(Continued)

(58) Field of Classification Search
CPC .................. H01Q 1/48; H01Q 1/273
See application file for complete search history.

(56) References Cited

U.S. PATENT DOCUMENTS 6,625,432 B1  9/2003 Araki
7,253,776 B2  8/2007 Miyagi
(Continued)

FOREIGN PATENT DOCUMENTS

JP   2005-223742 A   8/2005
JP   2006-166958 A   6/2006
(Continued)

OTHER PUBLICATIONS

International Search Report dated Nov. 28, 2017 issued in PCT/JP2017/034279.
(Continued)

*Primary Examiner* — Graham P Smith
(74) *Attorney, Agent, or Firm* — Scully, Scott, Murphy & Presser, P.C.

(57) ABSTRACT

A receiving antenna includes: an antenna element configured to receive a first radio signal for detecting a position of a capsule endoscope introduced into a subject and a second radio signal for transmitting an image captured by the capsule endoscope; a first ground connected to the antenna element; a plate on which the antenna element and the first ground are arranged; a first differential processing circuit configured to generate a differential signal based on the first and the second radio signals; a cable including one end connected to the first differential processing circuit to transmit the differential signal; a second ground provided along the cable; and a switch configured to open a path between the first ground and the second ground at a time of receiving the first radio signal, and short-circuit the path at a time of receiving the second radio signal.

6 Claims, 10 Drawing Sheets

(51) Int. Cl.
  *H04B 1/18* (2006.01)
  *A61B 1/00* (2006.01)
  H04N 5/225 (2006.01)
  *A61B 1/04* (2006.01)
  H04N 5/378 (2011.01)

(52) U.S. Cl.
  CPC .......... *A61B 1/00009* (2013.01); *A61B 1/041* (2013.01); *H04N 5/2256* (2013.01); *H04N 5/378* (2013.01)

(56) References Cited

U.S. PATENT DOCUMENTS

| | | |
|---|---|---|
| 8,022,891 B2 | 9/2011 | Leisten |
| 8,175,559 B2 | 5/2012 | Homan et al. |
| 2009/0318092 A1 | 12/2009 | Maoz et al. |
| 2017/0236622 A1 | 8/2017 | Yoshino et al. |

FOREIGN PATENT DOCUMENTS

| | | |
|---|---|---|
| JP | 2006-217582 A | 8/2006 |
| JP | 2007-124142 A | 5/2007 |
| JP | 2007-174540 A | 7/2007 |
| JP | 2009-543419 A | 12/2009 |
| JP | 2010-514241 A | 4/2010 |
| JP | 2013-223000 A | 10/2013 |
| JP | 2014-225784 A | 12/2014 |
| JP | 2015-122657 A | 7/2015 |
| WO | WO 99/62191 A1 | 12/1999 |
| WO | WO 2016/063520 A1 | 4/2016 |

OTHER PUBLICATIONS

Japanese Notification of Reasons for Refusal dated Apr. 3, 2018 issued in JP 2018-502020.

RECEIVING ANTENNA, RECEIVING ANTENNA UNIT, AND RECEIVING SYSTEM

CROSS-REFERENCE TO RELATED APPLICATION

This application is a continuation of PCT International Application No. PCT/JP2017/034279 filed on Sep. 22, 2017, which claims the benefit of priority from Japanese Patent Application No. 2016-202705, filed on Oct. 14, 2016, the entire contents of which are incorporated herein by reference.

BACKGROUND

The present disclosure relates to a receiving antenna, a receiving antenna unit, and a receiving system.

In the related art, endoscopes have been widely used as a medical observation device introduced into a body of a subject such as a patient to observe the inside of the subject. In recent years, a capsule endoscope, which is a swallow-type radio wave generator having in a casing an imaging device and a communication device for wirelessly transmitting an image signal captured by the imaging device to the outside of the body, has been developed. The capsule endoscope is swallowed from a patient's mouth for observation inside the subject, and then moves along the inside of organs such as esophagus, stomach, or small intestine by peristaltic movement of the organs to sequentially capture the inside until it is naturally excreted from the subject.

While the capsule endoscope moves inside the subject, images captured by the capsule endoscope are sequentially transmitted to the outside of the body via wireless communication, and are stored in a memory provided inside or outside the receiving device via an external receiving antenna unit, or are displayed on a display provided in the receiving device. A user such as a doctor or a nurse may obtain an image stored in the memory and store it in an information processing device using a cradle into which the receiving device is inserted, and may perform observation or diagnosis based on the image displayed on the display of the information processing device or the position of the capsule endoscope at the time of capturing of the corresponding image.

However, when the radio communication described above is performed, the antenna element of the receiving antenna unit is connected to, for example, a ground serving as a ground potential on a circuit board where a radio communication circuit is mounted (for example, see JP 2006-166958 A). Therefore, it is possible to adjust directivity or an impedance characteristic of the receiving antenna by connecting the antenna element and the ground.

There is a need for a receiving antenna, a receiving antenna unit, and a receiving system capable of improving position detection accuracy of the radio wave generator.

SUMMARY

A receiving antenna according to one aspect of the present disclosure includes: an antenna element configured to receive a first radio signal for detecting a position of a capsule endoscope introduced into a subject and a second radio signal for transmitting an image captured by the capsule endoscope, the first and the second radio signals being transmitted from the capsule endoscope; a first ground connected to the antenna element; a plate on which the antenna element and the first ground are arranged; a first differential processing circuit configured to generate a differential signal based on the first and the second radio signals received by the antenna element; a cable including one end connected to the first differential processing circuit to transmit the differential signal; a second ground provided along the cable; and a switch configured to open a path between the first ground and the second ground at a time of receiving the first radio signal, and short-circuit the path between the first ground and the second ground at a time of receiving the second radio signal.

The above and other features, advantages and technical and industrial significance of this invention will be better understood by reading the following detailed description of presently preferred embodiments of the disclosure, when considered in connection with the accompanying drawings.

DETAILED DESCRIPTION

Figure 1:
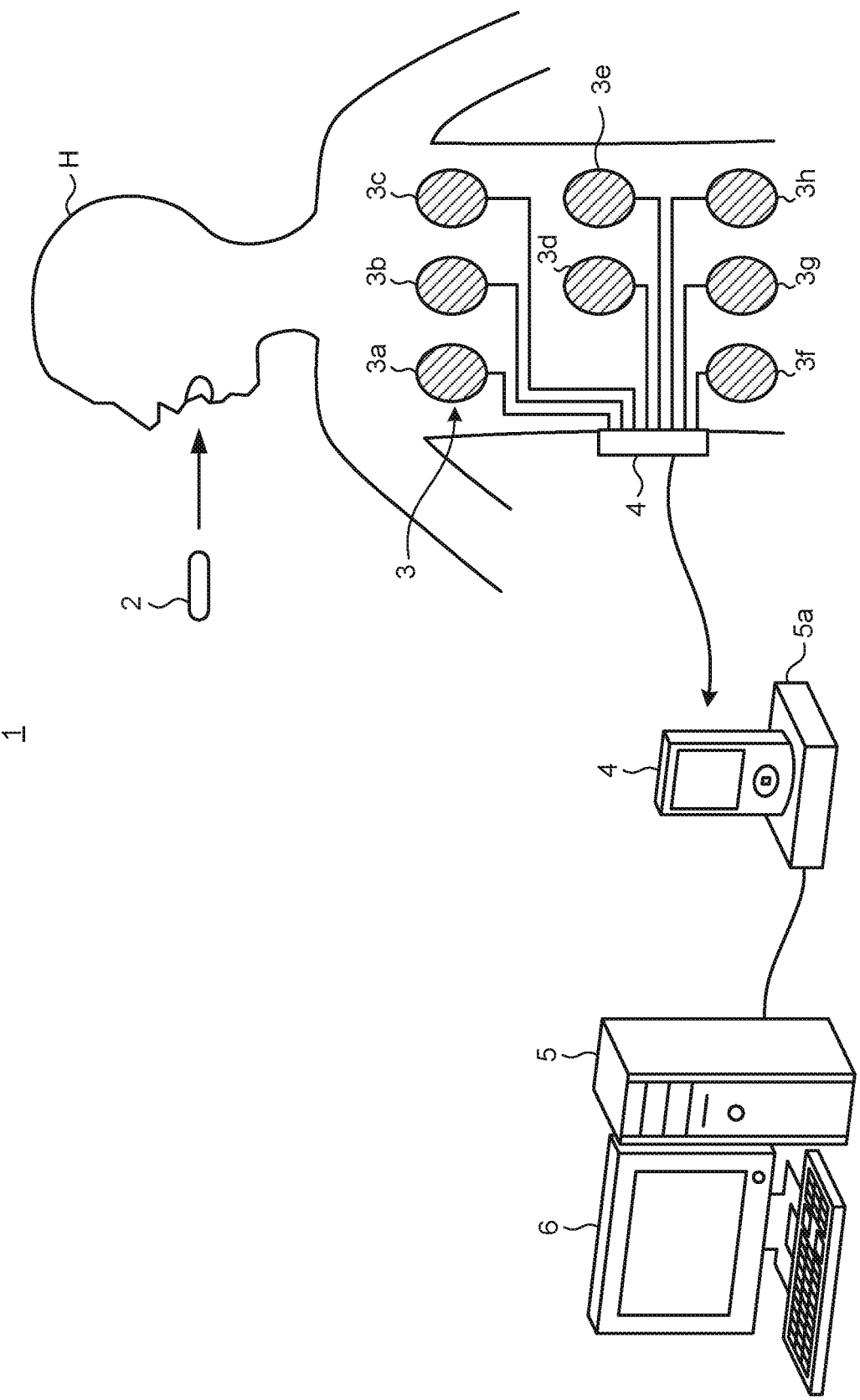
FIG. 1 is a schematic diagram illustrating a schematic configuration of a capsule endoscope system according to a first embodiment.

A capsule endoscope system using a medical capsule endoscope according to an embodiment will now be described. Note that, in the drawings, like reference numerals denote like elements. In addition, note that the drawings are schematic, and relationships between thickness and width of each element, scales of each member, or the like may be different from those of the reality.

First Embodiment

FIG. 1 is a schematic diagram illustrating a schematic configuration of a capsule endoscope system according to a first embodiment. As illustrated in FIG. 1, a capsule endoscope system 1 according to the first embodiment has a capsule endoscope 2 that is introduced into a subject H to create an image signal by capturing the inside of the subject H and serves as a radio wave transmitter for transmitting the image signal by overlapping with a radio signal on a radio wave, a receiving device 4 that receives the radio signal transmitted from the capsule endoscope 2 via a receiving antenna unit 3 having a plurality of receiving antennas 3a to 3h installed in the subject H, and a processing device 5 that receives the image signal captured by the capsule endoscope 2 from the receiving device 4 via a cradle 5a and processes the image signal to create an image inside the subject H. The image created by the processing device 5 is displayed and output, for example, from a display device 6. In the first embodiment, it is assumed that the receiving device 4 and at least one of the receiving antennas 3a to 3h constitute the receiving system.

Figure 2:
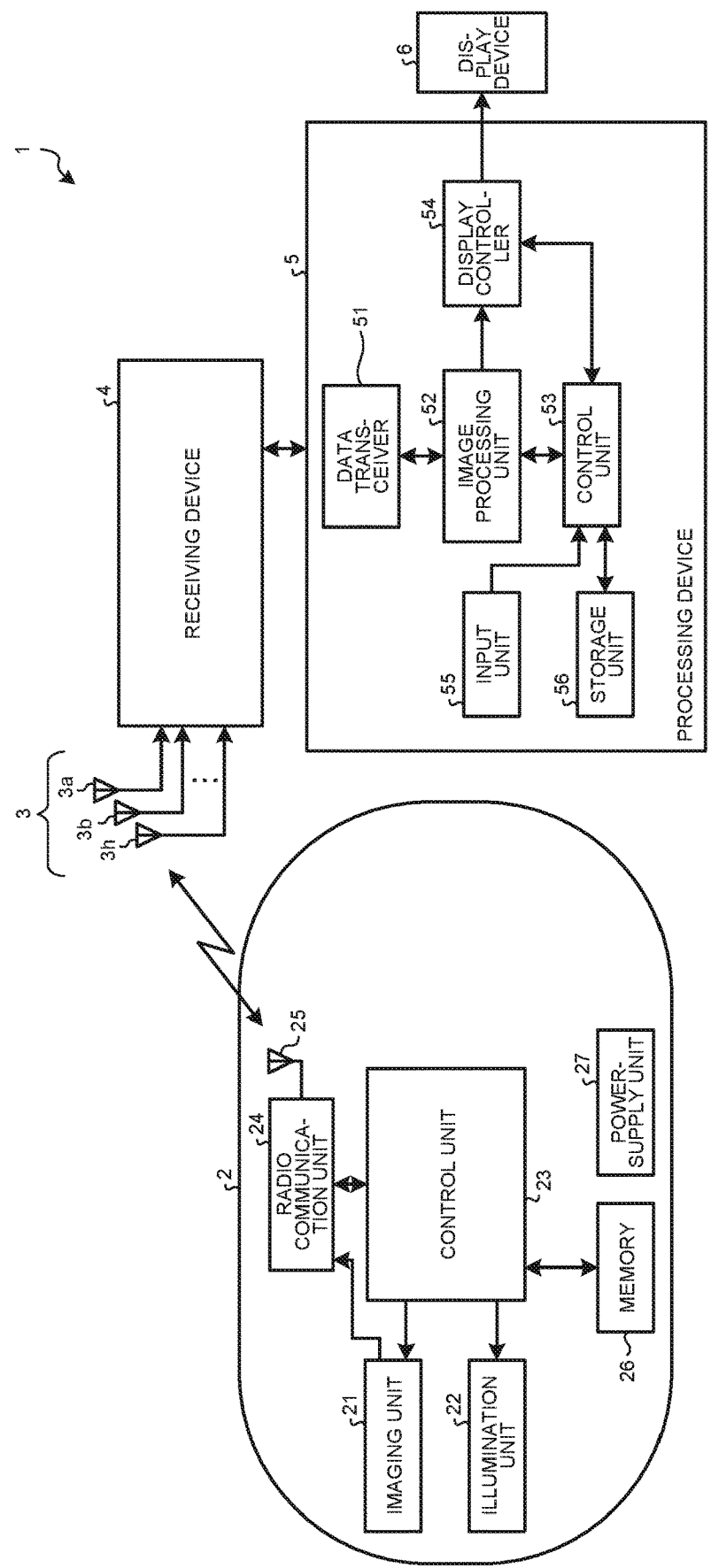
FIG. 2 is a block diagram illustrating a schematic configuration of the capsule endoscope system according to the first embodiment.

FIG. 2 is a block diagram illustrating a schematic configuration of the capsule endoscope system according to the first embodiment. The capsule endoscope 2 has an imaging unit 21, an illumination unit 22, a control unit 23, a radio communication unit 24, an antenna 25, a memory 26, and a power-supply unit 27. The capsule endoscope 2 is a device obtained by embedding each parts described above in a capsular casing sized to allow the subject H to swallow it.

The imaging unit 21 has an image sensor that creates and outputs an image signal obtained by capturing the inside of the subject H from an optical image focused on a light-receiving surface, and an optical system such as an objective lens arranged in the light-receiving surface side of the image sensor. The image sensor is a CCD image sensor or a CMOS image sensor, has a plurality of pixels arranged in a matrix shape to receive light from the subject H, and performs optoelectric conversion for the light received by the pixels to create an image signal. The imaging unit 21 reads pixel values of a plurality of pixels arranged in a matrix shape on a horizontal line basis, and creates an image signal including a plurality of line data having synchronization signals given to each horizontal line.

The illumination unit 22 includes a white LED or the like that generates white light as illumination light. Note that the white light may be generated by mixing light of a plurality of LEDs, laser light sources, or the like having different emission wavelength bands. In addition, the illumination unit 22 may include a xenon lamp, a halogen lamp, or the like.

The control unit 23 controls operation processing of each part of the capsule endoscope 2. For example, in a case where the imaging unit 21 performs a capturing processing, the control unit 23 controls the imaging unit 21 so as to perform exposure and reading of the image sensor and controls the illumination unit 22 so as to irradiate illumination light depending on an exposure timing of the imaging unit 21. The control unit 23 includes a general processor such as a central processing unit (CPU) or a dedicated processor such as an application specific integrated circuit (ASIC) having various operation circuits or the like for executing a particular function.

The radio communication unit 24 processes the image signal output from the imaging unit 21. The radio communication unit 24 performs A/D conversion and a predetermined signal processing for the image signal output from the imaging unit 21 to acquire a digital format image and transmits it from the antenna 25 to the outside by overlapping with a radio signal along with related information. The related information includes, for example, identification information (such as a serial number) allocated to identify an entity of the capsule endoscope 2.

The memory 26 stores an execution program and a control program for executing various operations of the control unit 23. In addition, the memory 26 may temporarily store the image or the like subjected to the signal processing of the radio communication unit 24. The memory 26 includes a random access memory (RAM), a read-only memory (ROM), or the like.

The power-supply unit 27 has a battery including a button battery or the like, a power circuit that boosts power from the battery, and a power switch that switches on/off state of the power-supply unit 27 and supplies power to each part inside the capsule endoscope 2 after the power switch is on. Note that the power switch may include a reed switch switched on or off, for example, by an external magnetic force, so that it is switched to an on-state by applying an external magnetic force to the capsule endoscope 2 before use of the capsule endoscope 2 (that is, before the subject H swallows the capsule endoscope 2).

As the subject H swallows such a capsule endoscope 2, the capsule endoscope 2 sequentially captures living body parts (such as esophagus, stomach, small intestine, or large intestine) in a predetermined cycle (for example, 0.5-second cycle) while moving inside a digestive canal of the subject H by peristaltic movement of the organs. Then, images obtained through this capturing operation are sequentially and wirelessly transmitted to the receiving device 4 via the receiving antenna unit 3 along with related information. At this time, the capsule endoscope 2 alternately transmits a radio signal containing the image information and a radio signal for position detection.

Figure 3:
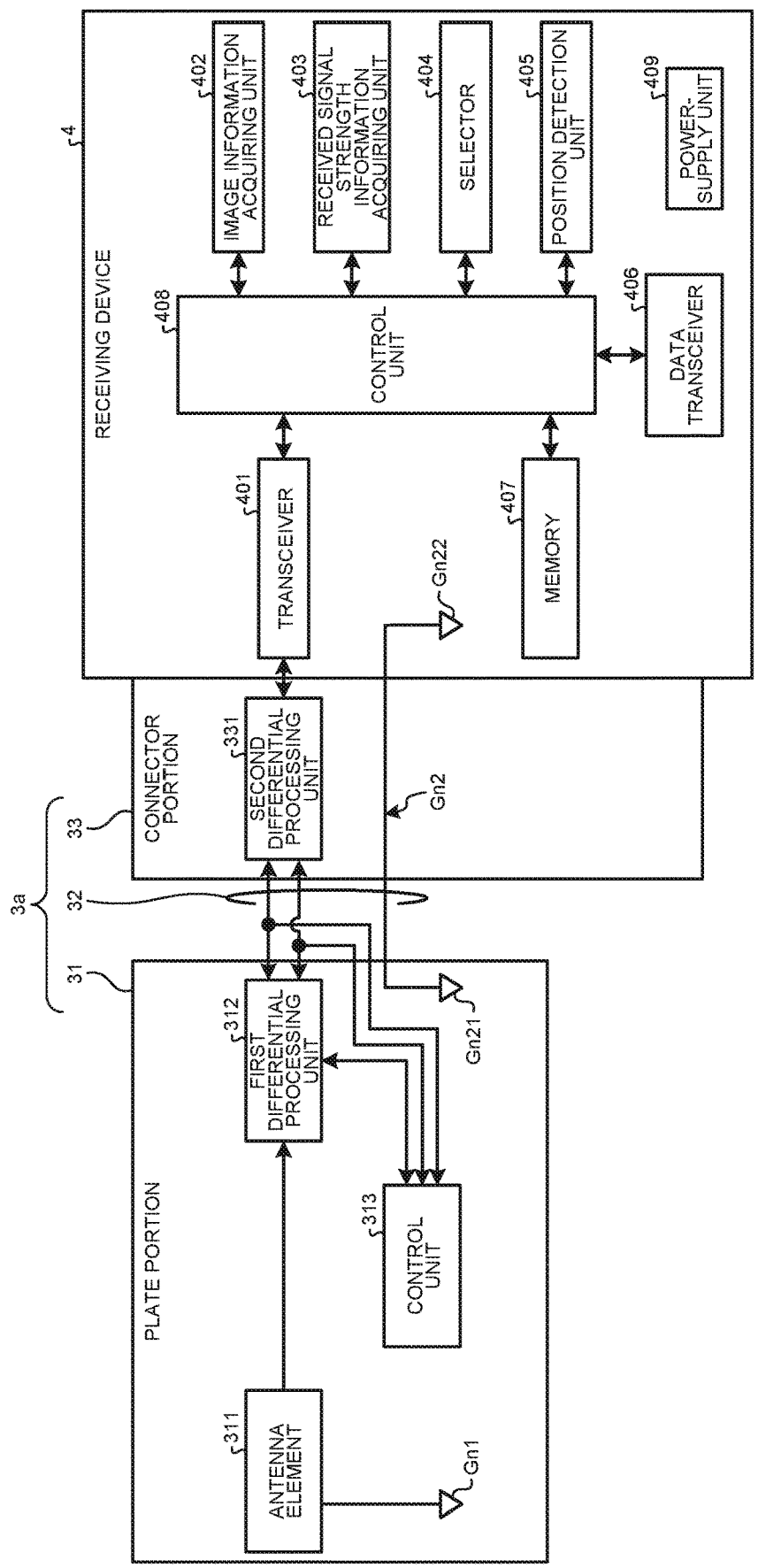
FIG. 3 is a block diagram illustrating a schematic configuration of a receiving system provided in the capsule endoscope system according to the first embodiment.

FIG. 3 is a block diagram illustrating a schematic configuration of a receiving system provided in the capsule endoscope system according to the first embodiment. In FIG. 3, a connection state between the receiving antenna 3a and the receiving device 4 will be described by way of example. The receiving antenna 3a has a plate-shaped plate portion 31 fixed to the subject H to receive the radio signal from the capsule endoscope 2, a cable portion 32 for integrating signal lines extending from the plate portion 31, and a connector portion 33 which is electrically connected to the cable portion 32 on the side opposite to the connecting side with the plate portion 31 and is electrically connected to the receiving device 4.

The plate portion 31 is fixed to a predetermined position on a body surface of the subject H using a well-known fixing means such as a belt or an adhesive sheet. The plate portion 31 includes an antenna element 311, a first differential processing unit 312, and a control unit 313. The plate portion 31 may have a single layer or a plurality of layers. The plate portion 31 is fixed to a human body surface, for example, depending on a path passing through the digestive canal.

The antenna element 311 receives the radio signal transmitted from the capsule endoscope 2 and outputs it to the first differential processing unit 312. In addition, the antenna element 311 is connected to a first ground Gn1 in order to adjust directivity or impedance characteristics of the antenna. The antenna element 311 may include a dipole antenna or a loop antenna. In a case where the plate portion 31 has a single layer, a connecting portion (electrode) between the antenna element 311 and the first ground Gn1 may be provided on the same surface or may be provided on different surfaces. Similarly, in a case where the plate portion 31 has a plurality of layers, a connecting portion (electrode) between the antenna element 311 and the first ground Gn1 may be provided on the same layer or may be provided on different layers. The connecting portion (electrode) of the first ground Gn1 may be provided in a region extending by projecting a main surface having the largest area of the plate provided with the antenna element 311 perpendicularly to the main surface.

On the plate portion 31, the antenna element 311 and the first ground Gn1 are arranged with their positions fixed. In addition, as described above, the plate portion 31 is fixed to a body surface of the subject H. For this reason, a distance between the antenna element 311 and the body surface of the subject H and a distance between the first ground Gn1 and the body surface of the subject H are maintained substantially constantly. Since the distance between the first ground Gn1 and the body surface of the subject H is maintained constantly, it is possible to suppress a variation of the characteristic of the receiving antenna.

The cable portion 32 integrates signal lines or the like that transmit the differential signal output from the first differential processing unit 312. In addition, the cable portion 32 has a second ground Gn2 connecting an antenna-side ground Gn21 provided in the plate portion 31 and a device-side ground Gn22 provided in the receiving device 4. The second ground Gn2 is electrically separated from the first ground Gn1, and includes a shield or the like, for example, provided in the cable portion 32. The second ground Gn2 is electrically connected to a signal transmission circuit (such as the first differential processing unit 312 or the control unit 313) formed in the plate portion 31.

The first differential processing unit 312 generates a differential signal based on the radio signal received by the antenna element 311, and outputs it to the cable portion 32. The first differential processing unit 312 is configured by combining an ASIC, a transformer, a differential amplifier, a balanced/unbalanced (balun) element, and the like.

The control unit 313 controls the operation processing of each part of the receiving antenna 3a. In addition, the control unit 313 receives a control signal from the receiving device 4 via the cable portion 32. The control unit 313 includes an ASIC or the like.

The connector portion 33 has a second differential processing unit 331. The second differential processing unit 331 performs processing for removing a common signal added to the differential signal received via the cable portion 32 and performs a differential processing to generate a single end signal containing image information without the common signal. The second differential processing unit 331 is configured by appropriately combining an ASIC, a differential amplifier, a balanced/unbalanced (balun) element, a common mode choke coil, or the like.

Although a configuration of the receiving antenna 3a has been described hereinbefore, this configuration may similarly apply to the receiving antennas 3b to 3h. Note that each connector portion 33 of the receiving antennas 3a to 3h may be connected to the receiving device 4 or may be provided in a single casing connected to the receiving device 4.

The receiving antenna unit 3 generates a differential signal from the radio signal received by the antenna element 311, transmits a signal to the cable portion 32 in response to this differential signal, and performs a differential processing for the differential signal in the connector portion 33 as a connecting portion with the receiving device 4 to convert it into a single end signal.

The receiving device 4 has a transceiver 401, an image information acquiring unit 402, a received signal strength information acquiring unit 403, a selector 404, a position detection unit 405, a data transceiver 406, a memory 407, a control unit 408, and a power-supply unit 409 that supplies power to each of these parts.

The transceiver 401 receives the single end signal (hereinafter, simply referred to as "signal") transmitted from the receiving antenna unit 3. In addition, the transceiver 401 performs a predetermined signal processing such as A/D conversion for the received signal. Furthermore, the transceiver 401 detects a reception strength (RSSI: received signal strength indicator) of the radio signal received by the receiving antennas 3a to 3h and outputs the received signal strength information. The transceiver 401 may detect and output a phase difference with the other radio signal instead of the radio field intensity. The transceiver 401 includes, for example, a CPU, an ASIC, or the like.

The image information acquiring unit 402 acquires the image information received by the transceiver 401. That is, the image information acquiring unit 402 acquires a plurality of pieces of image information received from the receiving antennas 3a to 3h. In addition, the image information acquiring unit 402 selects image information to be transmitted to the processing device 5 out of the acquired plurality of pieces of image information based on a selection result of the selector 404. The image information acquiring unit 402 stores the selected image information in the memory 407. Note that the related information included in the image information may contain the position information detected by the position detection unit 405 or the like. The image information acquiring unit 402 functions as an information selector for selecting the image information received from the receiving antennas 3a to 3h. The image information acquiring unit 402 includes a CPU, an ASIC, or the like.

The received signal strength information acquiring unit 403 acquires the received signal strength information output from the transceiver 401. That is, the received signal strength information acquiring unit 403 acquires each of the received signal strength information of the receiving antennas 3a to 3h. The received signal strength information acquiring unit 403 outputs each of the acquired received signal strength information of the receiving antennas 3a to 3h to the selector 404 and the position detection unit 405 via the control unit 408. The received signal strength information acquiring unit 403 includes a CPU, an ASIC, or the like.

The selector 404 selects the receiving antenna for acquiring the image information using each of the received signal strength information of the receiving antennas 3a to 3h input from the received signal strength information acquiring unit 403. Specifically, the selector 404 selects a receiving antenna having the strongest received signal strength out of the received signal strengths of the receiving antennas 3a to 3h. The selector 404 outputs a selection result to the image information acquiring unit 402 via the control unit 408. The selector 404 includes a CPU, an ASIC, or the like.

The position detection unit 405 performs computation for detecting a position of the capsule endoscope 2 using each of the received signal strength information of the receiving antennas 3a to 3h input from the transceiver 401. The position detection unit 405 outputs the position detection result of the capsule endoscope 2 to the control unit 408 as position information of the capsule endoscope 2 and stores it in the memory 407 in association with the image information selected by the image information acquiring unit 402. Alternatively, the position detection unit 405 may detect the position of the capsule endoscope 2 based on a method known in the art, such as JP 2007-283001 A, or may detect the position of the capsule endoscope 2 using a magnetic field for position detection. Furthermore, each of the received signal strength information may be stored in the memory 407 as the position information, and a computation function for position detection may be provided in the processing device 5. The position detection unit 405 may detect a position of the capsule endoscope 2 using a phase such as a phase difference with the other radio signal. The position detection unit 405 includes a CPU, an ASIC, or the like. Note that, in a case where a computation function for detection position is provided in the processing device 5, that is, in a case where the processing device 5 has the position detection unit 405, the received signal strength information acquiring unit 403 stores the received signal strength information in the memory 407 or transmits it to the processing device 5. Then, the position detection unit 405 of the processing device 5 performs position detection based on the received signal strength information acquired from the receiving device 4.

The data transceiver 406 transmits the image information and the related information stored in the memory 407 to the processing device 5 when it is communicably connected to the processing device 5. The data transceiver 406 includes a communication interface such as a USB or a LAN.

The memory 407 stores a program for executing various functions by operating the receiving device 4, the image information input from the image information acquiring unit 402, or the like. The memory 407 includes a RAM, a ROM, or the like.

The control unit 408 controls each part of the receiving device 4. The control unit 408 includes a CPU, an ASIC, or the like.

In addition, an operation unit as an input device used by a user to input various types of setting information or instruction information to the receiving device 4 may be provided.

Such a receiving device 4 is installed in and carried by the subject H during capturing of the capsule endoscope 2, for example, until the capsule endoscope 2 swallowed by the subject H is excreted through a digestive canal. The receiving device 4 stores the image information received via the receiving antenna unit 3 in the memory 407 in the meantime.

After the capturing of the capsule endoscope 2, the receiving device 4 is removed from the subject H and is set on a cradle 5a (see FIG. 1) connected to the processing device 5. As a result, the receiving device 4 is communicably connected to the processing device 5 to transmit (download) the image signal and the related information stored in the memory 407 to the processing device 5.

Returning to FIG. 2, the processing device 5 includes a work station having a display device 6 such as a liquid crystal display. The processing device 5 includes a data transceiver 51, an image processing unit 52, a control unit 53 that comprehensively controls each part, a display controller 54, an input unit 55, and a storage unit 56.

The data transceiver 51 is an interface connectable to a USB or a communication line such as a wired LAN or a wireless LAN, and has a USB port and a LAN port. According to an embodiment, the data transceiver 51 is connected to the receiving device 4 via the cradle 5a connected to the USB port to send/receive data to/from the receiving device 4.

The image processing unit 52 is implemented by hardware such as a CPU and performs a predetermined image processing for creating an in-vivo image corresponding to the image signal input from the data transceiver 51 or the image signal stored in the storage unit 56 by reading a predetermined program stored in the storage unit 56 described below.

The control unit 53 is implemented by a general processor such as CPU or a dedicated processor that includes various operation circuits to execute a particular function such as an ASIC, transmits an instruction or data to each part of the processing device 5 based on a signal input via the input unit 55 or the image signal input from the data transceiver 51 by reading various programs stored in the storage unit 56, and comprehensively controls operations of the entire processing device 5.

The display controller 54 performs a predetermined processing such as thinning of data or a gradation processing depending on an image display range of the display device 6 for the image created in the image processing unit 52, and displays and outputs the processed image to the display device 6.

The input unit 55 is implemented by, for example, an input device such as a keyboard, a mouse, a touch panel, or various switches. The input unit 55 receives an input of information or a command depending on a user's operation.

The storage unit 56 is implemented by a flash memory, a semiconductor memory such as a RAM or a ROM, a recording medium such as a HDD, an MO, a CD-R, or a DVD-R, a driving device for driving the recording medium, or the like. The storage unit 56 stores a program for executing various functions by operating the processing device 5, various types of information used in execution of the program, the image signal and the related information acquired via the receiving device 4, the in-vivo image created by the image processing unit 52, or the like.

According to the first embodiment described above, in the receiving antenna unit 3 that receives the radio signal received from the capsule endoscope 2, the first ground Gn1 connected to the antenna element 311 is separated from the second ground Gn2 connecting the antenna-side ground Gn21 provided in the plate portion 31 and the device-side ground Gn22 provided in the receiving device 4. In addition, a differential signal is generated from the radio signal received by the antenna element 311, and a signal is transmitted to the cable portion 32 using this differential signal, so that this signal is converted into a single end signal by performing a differential processing for the differential signal in the connector portion 33 which is a connecting part to the receiving device 4. As a result, it is possible to suppress a gain change, a directivity change, and an impedance change of the receiving antenna and suppress a change of the antenna characteristic that may deviate a reference position having the strongest receiving sensitivity. According to the first embodiment, the receiving device 4 uses a signal having deviation of the reference position of the receiving antenna suppressed, as the radio signal received by the receiving antenna unit 3 from the capsule endoscope 2. Therefore, it is possible to improve position detection accuracy of the capsule endoscope 2 which is a radio wave generator.

According to the first embodiment, in the cable portion 32 having a long transmission path, even when the shield serves as an antenna and a common signal is added, it is possible to remove the common signal through a differential processing of the second differential processing unit 331. According to the first embodiment, the receiving device 4 uses a signal that does not contain a common signal as the radio signal received by the receiving antenna unit 3 from the capsule endoscope 2. Therefore, it is possible to improve position detection accuracy of the capsule endoscope 2.

Note that, in the first embodiment described above, the radio signal for transmitting the image information from the capsule endoscope 2 and the radio signal for position detection are alternately and sequentially transmitted. Alternatively, position detection may be performed using the radio signal for transmitting the image information.

Although the second differential processing unit 331 performs the common signal removal processing and the differential processing in the first embodiment described above, a block for performing the differential processing and a block for removing the common signal from the differential signal may be provided independently. In a case where the blocks are independently provided, the block for performing the differential processing may include, for example, a differential amplifier, a balanced/unbalanced (balun) element, or the like, and the block for removing the common signal may include, for example, a common mode choke coil or the like.

Modification of First Embodiment

Figure 4:
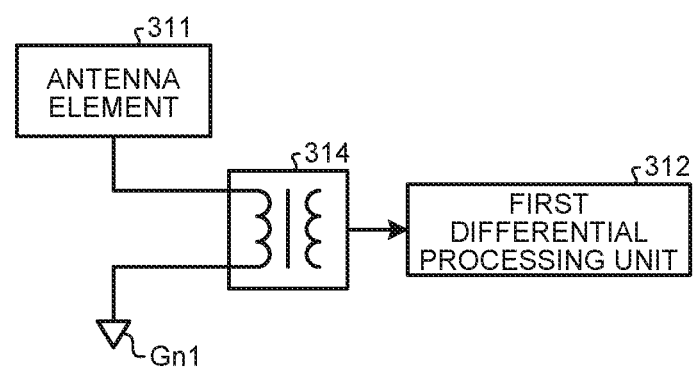
FIG. 4 is a schematic diagram illustrating configurations of main parts of a receiving system provided in a capsule endoscope system according to a modification of the first embodiment.

Subsequently, a modification of the first embodiment will be described. FIG. 4 is a schematic diagram illustrating configurations of main parts of a receiving system provided in a capsule endoscope system according to a modification of the first embodiment.

The receiving system according to this modification includes a transformer 314 provided between the antenna element 311 and the first differential processing unit 312 in the configuration of the plate portion 31 described above. Note that the first differential processing unit 312 according to this modification is configured by combining an ASIC, a differential amplifier, a balanced/unbalanced (balun) element, and the like.

The transformer 314 outputs the radio signal received by the antenna element 311 to the first differential processing unit 312. The transformer 314 is formed by winding primary and secondary coils around a magnetic core and transmits a pulse signal. In addition, the antenna element 311 and the first differential processing unit 312 are insulated by the primary and secondary coils.

According to the modification of the first embodiment described above, the transformer 314 is provided between the antenna element 311 and the first differential processing unit 312. Therefore, it is possible to electrically insulate the antenna element 311 connected to the first ground Gn1 and a signal transmission circuit such as the first differential processing unit 312 connected to the second ground Gn2.

Second Embodiment

Figure 5:
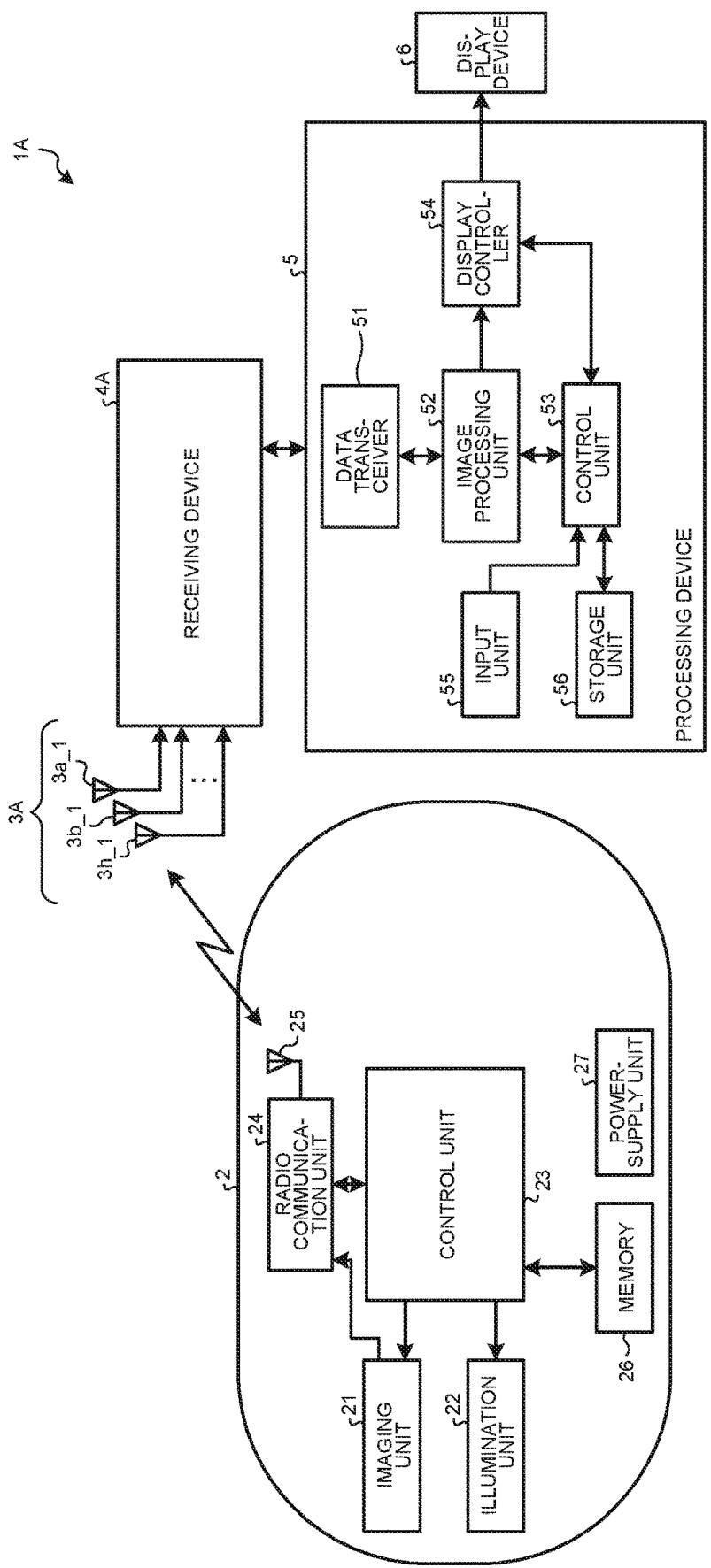
FIG. 5 is a block diagram illustrating a schematic configuration of a capsule endoscope system according to a second embodiment.

Subsequently, a second embodiment will be described. In the second embodiment, only differences from the first embodiment described above will be described. FIG. 5 is a block diagram illustrating a schematic configuration of a capsule endoscope system according to the second embodiment.

As illustrated in FIG. 5, a capsule endoscope system 1A according to the second embodiment has the capsule endoscope 2 described above, a receiving device 4A that receives a radio signal transmitted from the capsule endoscope 2 via a receiving antenna unit 3A having a plurality of receiving antennas 3a_1 to 3h_1 installed in the subject H (see FIG. 1), and a processing device 5 that receives the image signal captured by the capsule endoscope 2 from the receiving device 4A via the cradle 5a (see FIG. 1) and processes the image signal to create an image inside the subject H. In the second embodiment, it is assumed that the receiving system includes the receiving device 4A and at least one of the receiving antennas 3a_1 to 3h_1.

Figure 6:
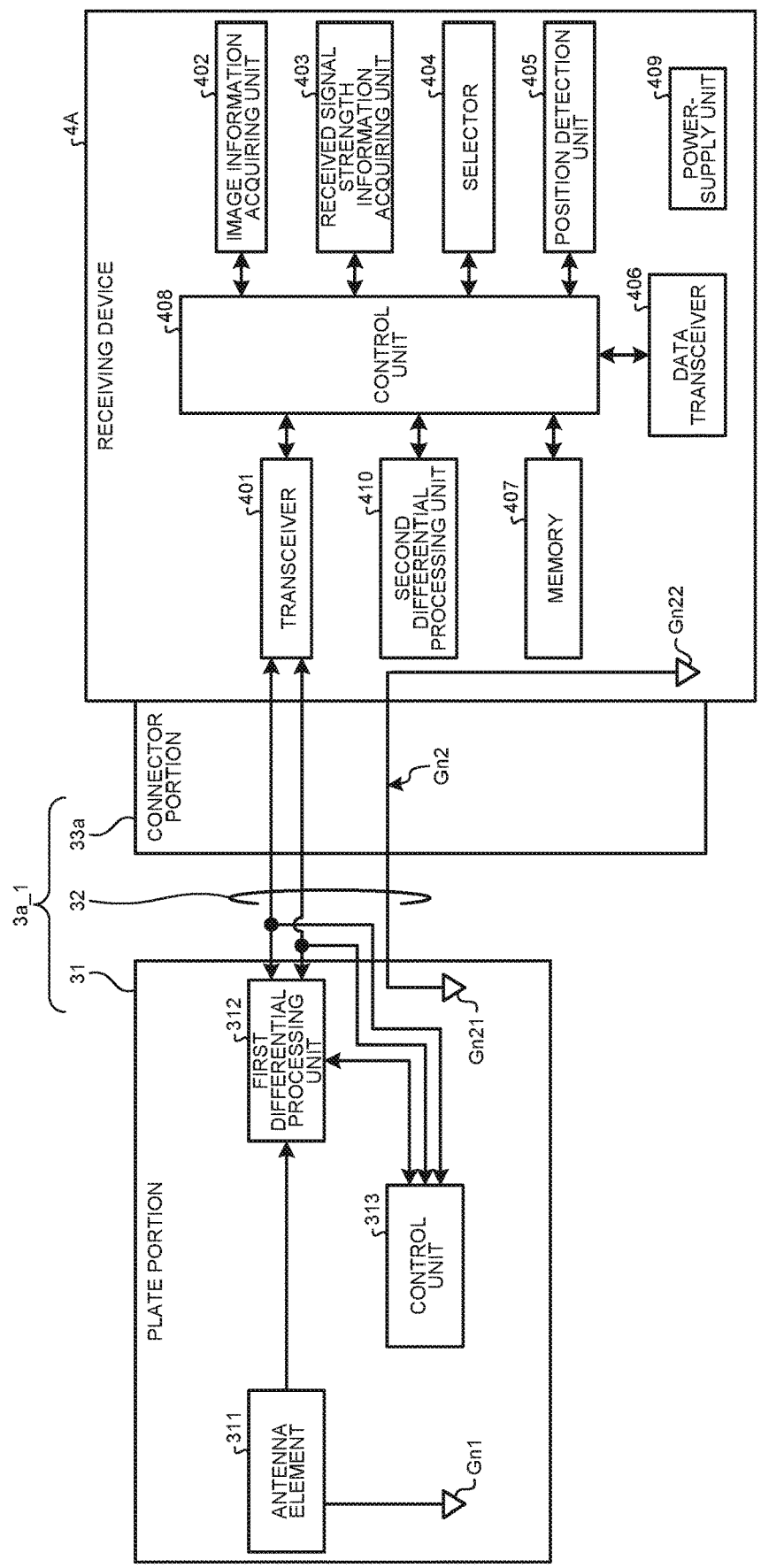
FIG. 6 is a block diagram illustrating a schematic configuration of a receiving system provided in the capsule endoscope system according to the second embodiment.

FIG. 6 is a block diagram illustrating a schematic configuration of a receiving system provided in the capsule endoscope system according to the second embodiment. In FIG. 6, a connection state between the receiving antenna 3a_1 and the receiving device 4A will be described by way of example. The receiving antenna 3a_1 includes the plate portion 31 and the cable portion 32 described above, and a connector portion 33a which is electrically connected to the cable portion 32 on the side opposite to the connecting side with the plate portion 31 and is electrically connected to the receiving device 4A.

The connector portion 33a outputs the differential signal received from the plate portion 31 via the cable portion 32 to the receiving device 4A. The connector portion 33a does not include the second differential processing unit 331 described above.

While the configuration of the receiving antenna 3a_1 has been described hereinbefore, this configuration may similarly apply to the receiving antennas 3b_1 to 3h_1. Note that each connector portion 33a of the receiving antennas 3a_1 to 3h_1 may be connected to the receiving device 4A, or may be provided in a single casing connected to the receiving device 4.

In the receiving antenna unit 3A, the differential signal is generated from the radio signal received by the antenna element 311, and this differential signal is output to the receiving device 4A via the cable portion 32 and the connector portion 33a.

The receiving device 4A has a second differential processing unit 410 in addition to the transceiver 401, the image information acquiring unit 402, the received signal strength information acquiring unit 403, the selector 404, the position detection unit 405, the data transceiver 406, the memory 407, the control unit 408, and the power-supply unit 409 described above.

The second differential processing unit 410 generates a single end signal containing the image signal and/or the received signal strength information by performing a differential processing for the differential signal received by the transceiver 401. The second differential processing unit 410 includes a CPU, an ASIC, or the like.

The receiving device 4A performs a differential processing for the differential signal received by the transceiver 401 to convert it into a single end signal. The image information acquiring unit 402 respectively acquires a signal subjected to the differential processing of the second differential processing unit 410.

In this manner, according to the second embodiment, the receiving antenna unit 3A outputs the differential signal generated from the received radio signal to the receiving device 4A, and the receiving device 4A converts this differential signal into a single end signal.

According to the second embodiment described above, the receiving antenna unit 3A that receives the radio signal received from the capsule endoscope 2 generates a differential signal from the radio signal received by the antenna element 311, and transmits a signal to the receiving device 4A using this differential signal via the cable portion 32 or the like. In addition, the receiving device 4A performs a differential processing for the differential signal to convert it into a single end signal. As a result, similar to the first embodiment described above, it is possible to suppress a deviation of the reference position of the receiving antenna. In addition, in the cable portion 32 having a long transmission path, even when the shield serves as an antenna and a common signal is added, it is possible to remove the common signal through the differential processing of the second differential processing unit 410. According to the second embodiment, it is possible to suppress a deviation of the reference position for the radio signal received by the receiving antenna unit 3A from the capsule endoscope 2, and transmit a signal having no common signal to the receiving device 4A. Furthermore, using this transmitted signal, it is possible to maintain position detection accuracy of the capsule endoscope 2 which is a radio wave generator.

Third Embodiment

Figure 7:
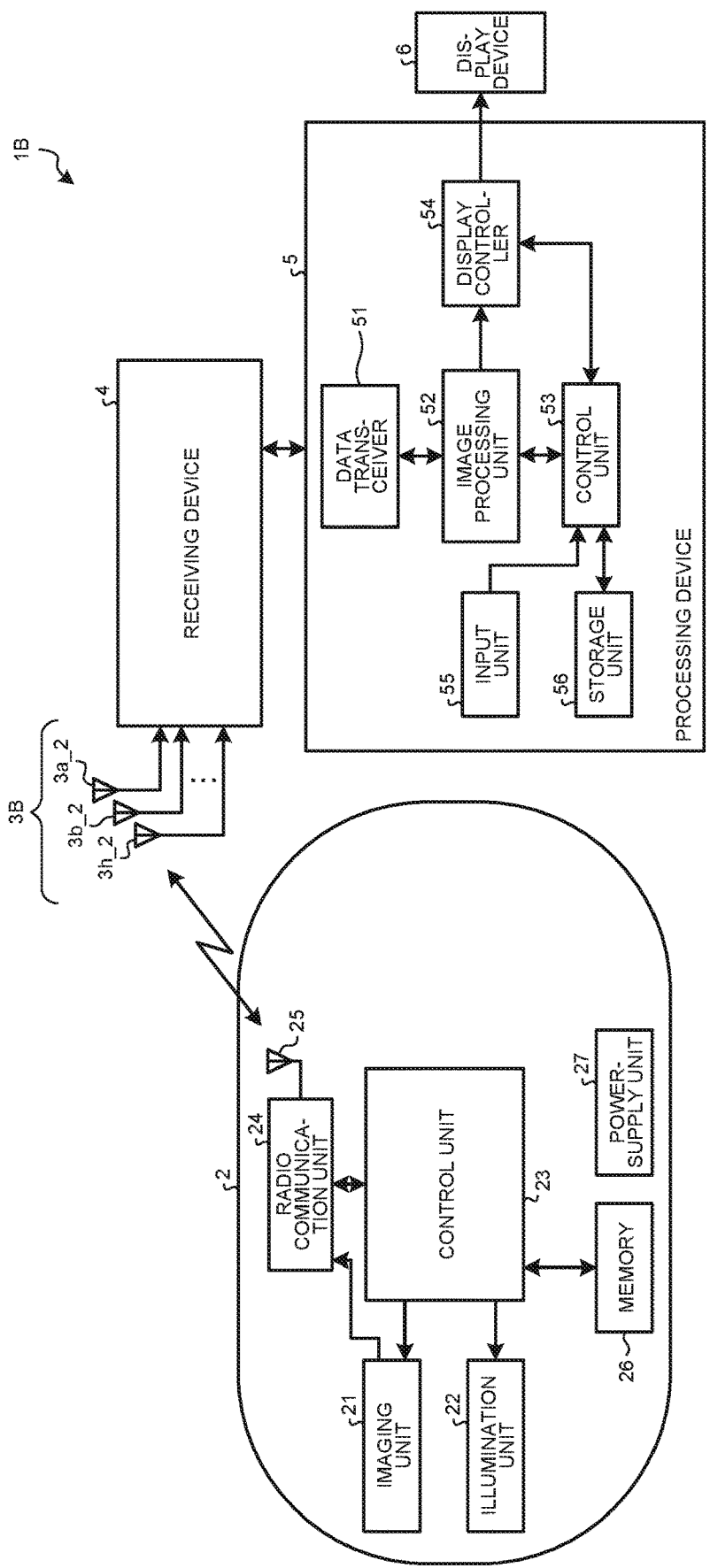
FIG. 7 is a block diagram illustrating a schematic configuration of a capsule endoscope system according to a third embodiment.

Subsequently, a third embodiment will be described. In the third embodiment, only differences from the first embodiment described above will be described. FIG. 7 is a block diagram illustrating a schematic configuration of a capsule endoscope system according to the third embodiment.

As illustrated in FIG. 7, a capsule endoscope system 1B according to the third embodiment has the capsule endoscope 2 described above, a receiving device 4 that receives the radio signal transmitted from the capsule endoscope 2 via a receiving antenna unit 3B having a plurality of receiving antennas $3a\_2$ to $3h\_2$ installed in the subject H (see FIG. 1), and a processing device 5 that receives an image signal captured by the capsule endoscope 2 from the receiving device 4 via the cradle $5a$ (see FIG. 1) and processes the image signal to create an image inside the subject H. In the third embodiment, it is assumed that the receiving device 4 and at least one of the receiving antennas $3a\_2$ to $3h\_2$ constitute a receiving system.

Figure 8:
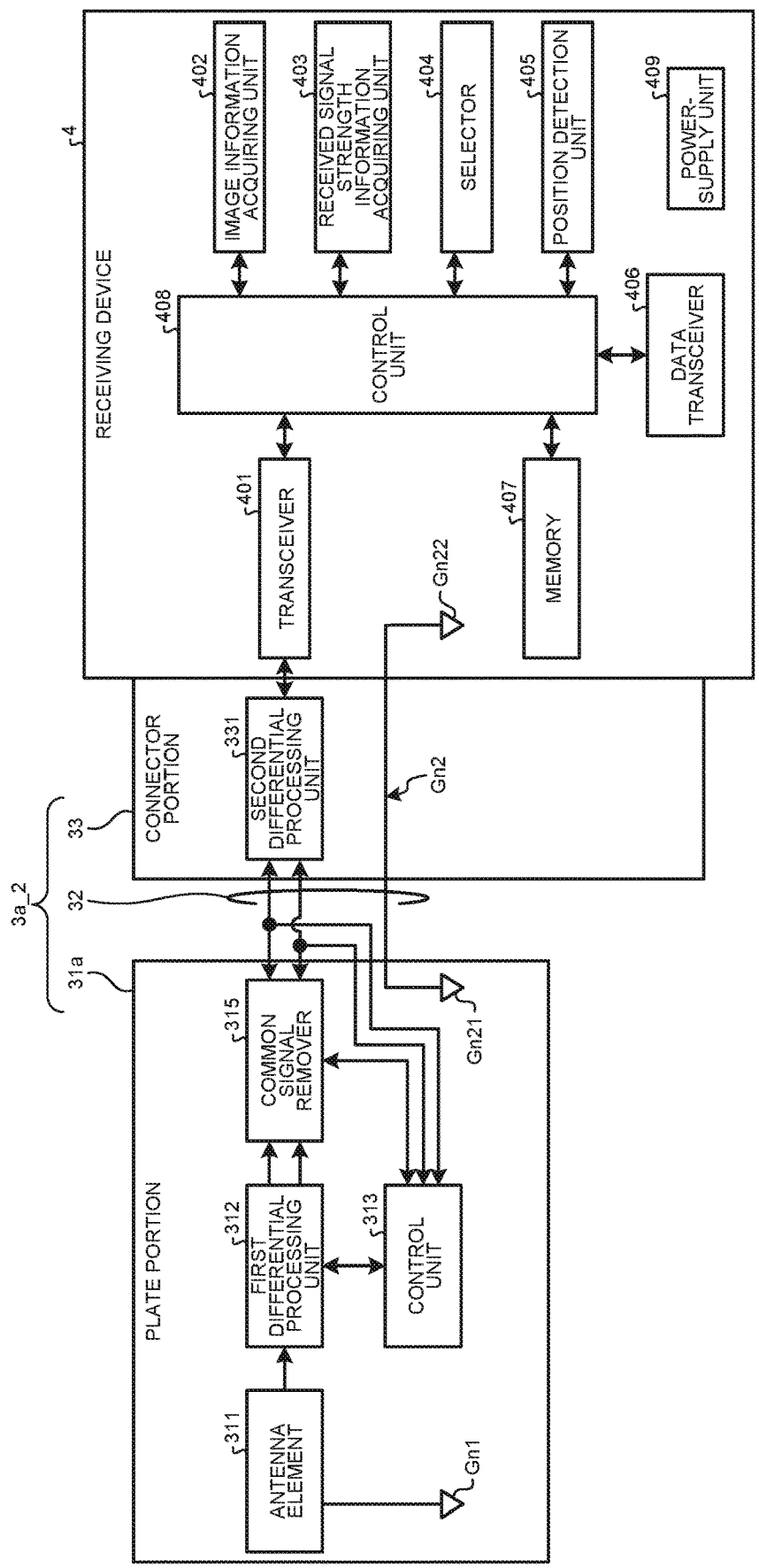
FIG. 8 is a block diagram illustrating a schematic configuration of a receiving system provided in the capsule endoscope system according to the third embodiment.

FIG. 8 is a block diagram illustrating a schematic configuration of a receiving system provided in the capsule endoscope system according to the third embodiment. In FIG. 8, a connection state between the receiving antenna $3a\_2$ and the receiving device 4 will be described by way of example. The receiving antenna $3a\_2$ has a plate portion $31a$ in addition to the cable portion 32 and the connector portion 33 described above.

The plate portion $31a$ has a common signal remover 315 in addition to the antenna element 311, the first differential processing unit 312, and the control unit 313 described above.

The common signal remover 315 outputs the differential signal generated by the first differential processing unit 312 to the cable portion 32 and performs a processing for removing the common signal transmitted in addition to the signal transmitted from the receiving device 4 via the cable portion 32, such as the control signal. As a result, it is possible to remove a common signal added to the transmission path of the receiving device 4 side, that is, a common signal (return signal) that may be input to the first differential processing unit 312. The common signal remover 315 includes, for example, a common mode choke coil or the like.

While the configuration of the receiving antenna $3a\_2$ has been described hereinbefore, this configuration may similarly apply to the receiving antennas $3b\_2$ to $3h\_2$. Note that each connector portion 33 of the receiving antennas $3a\_2$ to $3h\_2$ may be connected to the receiving device 4, or may be provided in a single casing connected to the receiving device 4.

According to the third embodiment described above, it is possible to obtain the effects of the first embodiment. In addition, since the common signal remover 315 removes the common signal (return signal) that is transmitted from the receiving device 4 side and may be input to the first differential processing unit 312, it is possible to perform the processing for generating the differential signal using the first differential processing unit 312 with higher accuracy.

Fourth Embodiment

Figure 9:
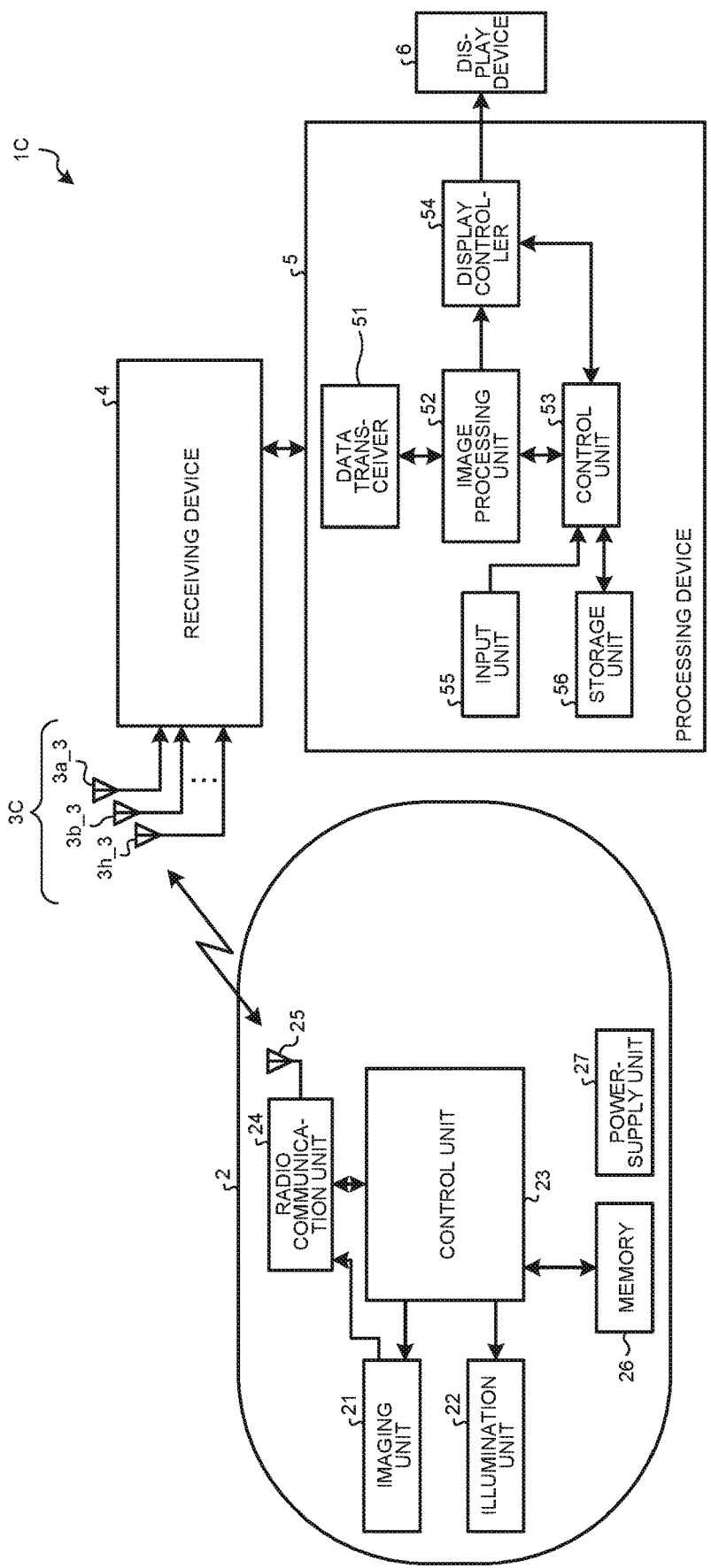
FIG. 9 is a block diagram illustrating a schematic configuration of a capsule endoscope system according to a fourth embodiment.

Subsequently, a fourth embodiment will be described. In the fourth embodiment, only differences from the first embodiment described above will be described. FIG. 9 is a block diagram illustrating a schematic configuration of a capsule endoscope system according to the fourth embodiment.

As illustrated in FIG. 9, a capsule endoscope system 1C according to the fourth embodiment has the capsule endoscope 2 described above, a receiving device 4 that receives the radio signal transmitted from the capsule endoscope 2 via a receiving antenna unit 3C having a plurality of receiving antennas $3a\_3$ to $3h\_3$ installed in the subject H (see FIG. 1), and a processing device 5 that receives the image signal captured by the capsule endoscope 2 from the receiving device 4 via the cradle $5a$ (see FIG. 1) and processes this image signal to create an image inside the subject H. In the fourth embodiment, it is assumed that the receiving device 4 and at least one of the receiving antennas $3a\_3$ to $3h\_3$ constitute a receiving system.

Figure 10:
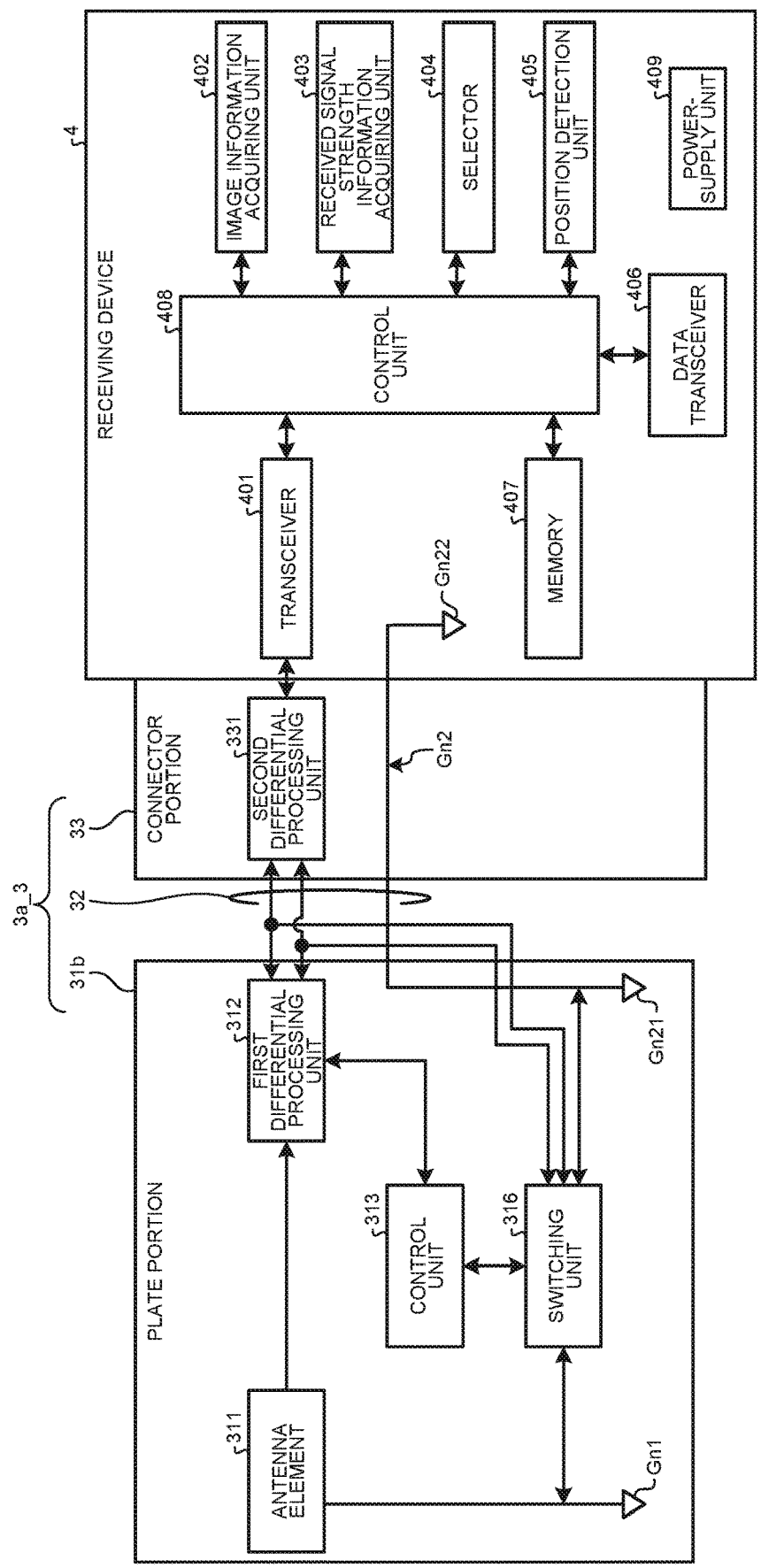
FIG. 10 is a block diagram illustrating a schematic configuration of a receiving system provided in the capsule endoscope system according to the fourth embodiment.

FIG. 10 is a block diagram illustrating a schematic configuration of a receiving system provided in the capsule endoscope system according to the fourth embodiment. In FIG. 10, a connection state between the receiving antenna $3a\_3$ and the receiving device 4 will be described by way of example. The receiving antenna $3a\_3$ has a plate portion $31b$ in addition to the cable portion 32 and the connector portion 33 described above.

The plate portion $31b$ has a switching unit 316 in addition to the antenna element 311, the first differential processing unit 312, and the control unit 313 described above.

The switching unit 316 switches a connection state between the first ground Gn1 connected to the antenna element 311 and the second ground Gn2 supplied from the receiving device 4 to the plate portion $31b$ via the cable portion 32. Specifically, the switching unit 316 opens or short-circuits a path between the first and second grounds Gn1 and Gn2. Here, "open" refers to an electrically disconnected state in a circuit.

While the configuration of the receiving antenna $3a\_3$ has been described hereinbefore, this configuration may similarly apply to the receiving antennas $3b\_3$ to $3h\_3$. Note that each connector portion 33 of the receiving antennas $3a\_3$ to $3h\_3$ may be connected to the receiving device 4, or may be provided in a single casing connected to the receiving device 4.

The control unit 408 of the receiving device 4 determines whether the radio signal received by the transceiver 401 is for transmitting image information or for detecting a position of the capsule endoscope 2, and outputs a control signal for the switching unit 316 to the transceiver 401 based on a result of the determination. Specifically, if the radio signal to be received in the next time is for position detection, the control unit 408 outputs a first control signal for opening a path between the first ground Gn1 and the second ground Gn2. If the radio signal to be received in the next time is for transmitting image information, the control unit 408 outputs a second control signal for short-circuiting the path between the first ground Gn1 and the second ground Gn2. As a control of the switching unit 316 using the control unit 408, for example, voltages applied in the first control and the second control may be set to be different, or clocks of the received signals may be set to be different. The transceiver 401 transmits a control signal to the control unit 313 via the cable portion 32. The control unit 313 causes the switching unit 316 to perform switching based on the control signal from the control unit 408. Alternatively, the transceiver 401 may directly transmit the control signal to the switching unit 316 via the cable portion 32 to cause the switching unit 316 to perform the switching.

As the control signal is received via the cable portion 32 or the like, the switching unit 316 switches the connection state between the first and second grounds Gn1 and Gn2 based on the control signal. In a case where a path between the first and second grounds Gn1 and Gn2 is short-circuited, the second ground Gn2 of the cable portion 32 also serves as a receiving antenna, so that a high gain can be obtained while the stability of the characteristic of the differential signal is degraded. In comparison, in a case where the path between the first and second grounds Gn1 and Gn2 is opened, the antenna element 311 is electrically separated from the cable portion 32 or the like, and only the antenna element 311 functions as a receiving antenna. For this reason, in comparison with a case where the path between grounds is short-circuited, the obtained gain is small, but the characteristic is stabilized. Therefore, it is possible to stabilize the reference position of the receiving antenna.

According to the fourth embodiment described above, it is possible to obtain the effects of the first embodiment. In addition, in a case where image information is acquired, it is possible to obtain a high gain by short-circuiting the path between the first and second grounds Gn1 and Gn2. In a case where a position of the capsule endoscope 2 is detected, the characteristic is stabilized by opening the path between the first and second grounds Gn1 and Gn2, so that it is possible to stabilize the reference position of the receiving antenna. According to the fourth embodiment, it is possible to improve position detection accuracy while securing the capability of receiving the image information by switching a connection state between the first and second grounds Gn1 and Gn2.

Note that, in the fourth embodiment described above, the switching unit 316 is controlled by the control unit 408 of the receiving device 4 so as to switch a connection state between the first and second grounds Gn1 and Gn2. Alternatively, the control unit 313 may determine whether the radio signal received by the antenna element 311 is for transmitting image information or for detecting the position of the capsule endoscope 2, and output the control signal for the switching unit 316 based on a result of the determination. In addition, a control unit 313 for controlling the switching unit 316 may be provided in the connector portion 33 of the receiving antenna to perform a switching control of the switching unit 316.

While the embodiments have been described hereinbefore, the embodiments and the modifications described above are not intended to limit the scope. The disclosure is not limited by the embodiments and the modifications described above, and various embodiments may be included without departing from the spirit and scope as specified in the appended claims. The configurations of the embodiments and modifications may be suitably combined.

Execution programs for each processing executed by each part of the capsule endoscopes 2, the receiving antenna units 3 to 3C, the receiving devices 4 and 4A, and the processing devices 5 in the capsule endoscope systems 1 to 1C according to the first to fourth embodiments may be provided as a file having an installable or executable format by recording it on a computer-readable recording medium such as a CD-ROM, a flexible disk (FD), a CD-R, and a DVD. Alternatively, the execution programs may be stored in a computer connected to a network such as the Internet and provided by downloading it via the network. In addition, the execution programs may be provided or distributed via a network such as the Internet.

In the first to fourth embodiments, the radio signal is generated and output by the capsule endoscope 2 as a radio wave transmitter. However, any unit may be employed without limiting to the capsule endoscope 2 as long as it can generate and output the radio signal. For example, a catheter or the like capable of generating and outputting the radio signal may be employed as the radio wave transmitter.

As described above, the receiving antenna, the receiving antenna unit, the receiving system, and the receiving device according to the present disclosure are suitable for improving position detection accuracy of the radio wave generator.

According to the present disclosure, it is possible to improve the position detection accuracy of the radio wave generator.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving antenna comprising:
    an antenna element configured to receive a first radio signal for detecting a position of a capsule endoscope introduced into a subject and a second radio signal for transmitting an image captured by the capsule endoscope, the first and the second radio signals being transmitted from the capsule endoscope;
    a first ground connected to the antenna element;
    a plate on which the antenna element and the first ground are arranged;
    a first differential processing circuit configured to generate a differential signal based on the first and the second radio signals received by the antenna element;
    a cable including one end connected to the first differential processing circuit to transmit the differential signal;
    a second ground provided along the cable; and
    a switch configured to
        open a path between the first ground and the second ground at a time of receiving the first radio signal, and
        short-circuit the path between the first ground and the second ground at a time of receiving the second radio signal.

2. The receiving antenna according to claim 1, further comprising a connector portion connected to an end of the cable opposite to the plate and electrically connected to an external device,
    wherein the connector portion includes a second differential processing circuit configured to convert the differential signal into a single end signal.

3. The receiving antenna according to claim 1, wherein the plate portion is fixed to a predetermined position on a surface of the subject.

4. The receiving antenna according to claim 1, wherein the antenna element and an electrode of the first ground are arranged within a region extending by projecting a main surface having a largest area of the plate in a direction perpendicular to the main surface.

5. A receiving antenna unit comprising a plurality of the receiving antennas according to claim 1.

6. A receiving system comprising:
   at least one receiving antenna including
      an antenna element configured to receive a first radio signal for detecting a position of a capsule endoscope introduced into a subject and a second radio signal for transmitting an image captured by the capsule endoscope, the first and the second radio signals being transmitted from the capsule endoscope,
      a first ground connected to the antenna element,
      a plate on which the antenna element and the first ground are arranged,
      a first differential processing circuit configured to generate a differential signal based on the first or the second radio signal received by the antenna element,
      a cable including one end connected to the first differential processing circuit to transmit the differential signal,
      a second ground provided along the cable, and
      a switch configured to
         open a path between the first ground and the second ground at a time of receiving the first radio signal, and
         short-circuit the path between the first ground and the second ground at a time of receiving the second radio signal;
   a receiving device including a receiver configured to receive the differential signal from the receiving antenna; and
   a second differential processing circuit provided in any one of the receiving antenna or the receiving device to convert the differential signal into a single end signal.

* * * * *